US008486427B2

(12) United States Patent
Colman et al.

(10) Patent No.: US 8,486,427 B2
(45) Date of Patent: Jul. 16, 2013

(54) WIPE FOR USE WITH A GERMICIDAL SOLUTION

(75) Inventors: Charles W. Colman, Marietta, GA (US); Marsha R. Forthofer, Woodstock, GA (US); Mark B. Majors, Cumming, GA (US); Dennis L. Hasha, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 138 days.

(21) Appl. No.: 13/025,623

(22) Filed: Feb. 11, 2011

(65) Prior Publication Data

US 2012/0207805 A1    Aug. 16, 2012

(51) Int. Cl.
*A01N 25/34* (2006.01)
*A01N 33/12* (2006.01)

(52) U.S. Cl.
USPC .......................................... 424/404; 514/642

(58) Field of Classification Search
USPC .......................................... 424/404; 514/642
See application file for complete search history.

(56) References Cited

U.S. PATENT DOCUMENTS

| | | | |
|---|---|---|---|
| 2,182,306 A | 12/1939 | Ulrich et al. | |
| 2,208,095 A | 7/1940 | Esselmann et al. | |
| 2,553,696 A | 5/1951 | Wilson | |
| 2,648,635 A | 8/1953 | Brown et al. | |
| 2,806,839 A | 9/1957 | Crowther | |
| 3,033,746 A | 5/1962 | Moyle et al. | |
| 3,338,992 A | 8/1967 | Kinney | |
| 3,341,394 A | 9/1967 | Kinney | |
| 3,494,821 A | 2/1970 | Evans | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,719,711 A | 3/1973 | Temple | |
| 3,802,817 A | 4/1974 | Matsuki et al. | |
| 3,849,241 A | 11/1974 | Butin et al. | |
| 3,954,113 A | 5/1976 | Bohrer et al. | |
| 3,965,026 A | 6/1976 | Lancz | |
| 4,100,324 A | 7/1978 | Anderson et al. | |
| 4,144,123 A * | 3/1979 | Scharf et al. | 162/164.3 |
| 4,144,370 A | 3/1979 | Boulton | |
| 4,340,563 A | 7/1982 | Appel et al. | |
| 4,441,962 A | 4/1984 | Osborn, III | |
| 4,795,668 A | 1/1989 | Krueger et al. | |
| 4,885,102 A | 12/1989 | Yamamura et al. | |
| 4,969,976 A * | 11/1990 | Reed | 162/164.3 |
| 5,057,361 A | 10/1991 | Sayovitz et al. | |
| 5,057,368 A | 10/1991 | Largman et al. | |
| 5,069,970 A | 12/1991 | Largman et al. | |
| 5,108,820 A | 4/1992 | Kaneko et al. | |
| 5,162,074 A | 11/1992 | Hills | |
| 5,223,096 A | 6/1993 | Phan et al. | |
| 5,277,976 A | 1/1994 | Hogle et al. | |
| 5,284,703 A | 2/1994 | Everhart et al. | |
| 5,336,552 A | 8/1994 | Strack et al. | |
| 5,350,624 A | 9/1994 | Georger et al. | |
| 5,382,400 A | 1/1995 | Pike et al. | |
| 5,421,898 A * | 6/1995 | Cavanagh | 134/7 |
| 5,466,410 A | 11/1995 | Hills | |
| 5,487,813 A | 1/1996 | Vinson et al. | |
| 5,536,370 A | 7/1996 | Scherr et al. | |
| 5,641,855 A | 6/1997 | Scherr et al. | |
| 5,785,179 A | 7/1998 | Buczwinski et al. | |
| 5,814,188 A | 9/1998 | Vinson et al. | |
| 5,908,707 A | 6/1999 | Cabell et al. | |
| 5,935,883 A | 8/1999 | Pike | |
| 5,942,588 A | 8/1999 | Ettl et al. | |
| 5,964,351 A | 10/1999 | Zander | |

(Continued)

FOREIGN PATENT DOCUMENTS

| | | |
|---|---|---|
| GB | 1509967 | 5/1978 |
| JP | 2003073694 | 3/2003 |

(Continued)

OTHER PUBLICATIONS

Search Report and Written Opinion for PCT/IB2012/050201 dated Aug. 1, 2012, 10 pages.
Article—Alakomi et al., "Weakening Effect of Cell Permeabilizers on Gram-Negative Bacteria Causing Biodeterioration," *Applied and Environmental Microbiology*, vol. 72, No. 7, Jul. 2006, pp. 4695-4703.
Article—Axelson et al., "Multinuclear ($^{13}$C, $^{15}$N) NMR Study of Polyethyleneimine-Based Polymers," Journal of Polymer Science: Polymer Chemistry Edition, vol. 23, 1985, pp. 2507-2525.

(Continued)

*Primary Examiner* — Blessing Fubara
*Assistant Examiner* — Jennifer Berrios
(74) *Attorney, Agent, or Firm* — Dority & Manning, P.A.

(57) ABSTRACT

An antimicrobial wipe that contains a polymer coating having a synergistic combination of ingredients for providing controlled release of an antimicrobial agent and also good antimicrobial efficacy is provided. One such ingredient is a high molecular weight polyamideamine release agent. Due to the polycationic nature of the release agent, it is able to adhere to the wipe, which is generally formed from fibers having a negative surface charge (e.g., cellulosic fibers). In this manner, the release agent can occupy binding sites on the wipe to inhibit the antimicrobial agent from adhering thereto, thus allowing it to be expressed in the germicidal solution to kill microbes on the desired surface. The adherence of the release agent to the wipe is even further enhanced by crosslinking the polyamideamine to increase its molecular weight, thereby enabling it to form a structural network that physically adheres to the wipe and that blocks the antimicrobial agent from binding thereto. Furthermore, the polyamideamine is amidated so that it contains secondary and/or tertiary amides. A cell permeabilizer is also employed in the polymer coating to enhance the efficacy of the antimicrobial agent during use. More particularly, polycationic materials are particularly useful in permeabilizing the outer cell membrane without adversely impacting the ability of the polyamideamine to release the antimicrobial agent within the wipe.

26 Claims, No Drawings

U.S. PATENT DOCUMENTS

| | | | |
|---|---|---|---|
| 5,981,044 | A | 11/1999 | Phan et al. |
| 5,989,004 | A | 11/1999 | Cook |
| 6,030,331 | A | 2/2000 | Zander |
| 6,045,817 | A | 4/2000 | Ananthapadmanabhan et al. |
| 6,056,967 | A | 5/2000 | Steuerle et al. |
| 6,144,123 | A | 11/2000 | Selci |
| 6,153,208 | A * | 11/2000 | McAtee et al. ............... 424/402 |
| 6,158,614 | A | 12/2000 | Haines et al. |
| 6,200,669 | B1 | 3/2001 | Marmon et al. |
| 6,201,695 | B1 | 3/2001 | Duesman et al. |
| 6,217,889 | B1 | 4/2001 | Lorenzi et al. |
| 6,235,940 | B1 | 5/2001 | Mohr et al. |
| 6,269,969 | B1 | 8/2001 | Huang et al. |
| 6,269,970 | B1 | 8/2001 | Huang et al. |
| 6,273,359 | B1 | 8/2001 | Newman et al. |
| 6,300,304 | B1 | 10/2001 | Boeckh et al. |
| 6,315,864 | B2 | 11/2001 | Anderson et al. |
| 6,458,343 | B1 | 10/2002 | Zeman et al. |
| 6,547,928 | B2 | 4/2003 | Barnholtz et al. |
| 6,559,116 | B1 | 5/2003 | Godfroid et al. |
| 6,607,637 | B1 | 8/2003 | Vinson et al. |
| 6,673,761 | B2 | 1/2004 | Mitra et al. |
| 6,716,311 | B1 | 4/2004 | Decker et al. |
| 6,730,654 | B2 | 5/2004 | Godfroid et al. |
| 6,755,939 | B2 | 6/2004 | Vinson et al. |
| 6,797,117 | B1 | 9/2004 | McKay et al. |
| 6,855,229 | B2 | 2/2005 | McKay et al. |
| 6,986,897 | B1 | 1/2006 | Roberts et al. |
| 7,048,806 | B2 | 5/2006 | Ochomogo et al. |
| 7,282,116 | B2 | 10/2007 | Vinson et al. |
| 7,311,853 | B2 | 12/2007 | Vinson et al. |
| 7,432,234 | B2 | 10/2008 | Ochomogo et al. |
| 7,432,309 | B2 | 10/2008 | Vinson |
| 7,576,047 | B2 | 8/2009 | Kilkenny et al. |
| 7,687,027 | B2 | 3/2010 | McGill |
| 7,736,525 | B2 | 6/2010 | Thankachan et al. |
| 7,741,263 | B2 | 6/2010 | Kilkenny et al. |
| 7,790,217 | B2 | 9/2010 | Toreki et al. |
| 7,838,447 | B2 | 11/2010 | Clark et al. |
| 2002/0031486 | A1 | 3/2002 | Lunsmann et al. |
| 2002/0183233 | A1 | 12/2002 | Mitra et al. |
| 2003/0100465 | A1 | 5/2003 | Kilkenny et al. |
| 2003/0109411 | A1 | 6/2003 | Kilkenny et al. |
| 2003/0127206 | A1 | 7/2003 | Barnholtz et al. |
| 2003/0157856 | A1 | 8/2003 | Schroeder et al. |
| 2004/0188045 | A1 | 9/2004 | McKay et al. |
| 2006/0052269 | A1 | 3/2006 | Panandiker et al. |
| 2006/0166849 | A1 | 7/2006 | Kilkenny et al. |
| 2007/0037721 | A1 | 2/2007 | Michels et al. |
| 2007/0137811 | A1 | 6/2007 | Runge et al. |
| 2008/0107698 | A1 | 5/2008 | Luu et al. |
| 2008/0163437 | A1 | 7/2008 | Fang et al. |
| 2009/0197247 | A1 | 8/2009 | Ribault et al. |
| 2009/0215052 | A1 | 8/2009 | Marc et al. |
| 2010/0261634 | A1 | 10/2010 | Misske et al. |

FOREIGN PATENT DOCUMENTS

| | | |
|---|---|---|
| WO | WO 9412560 | 6/1994 |
| WO | WO 9606152 | 2/1996 |
| WO | WO 9606153 | 2/1996 |
| WO | WO 9720879 | 6/1997 |

OTHER PUBLICATIONS

Article—Dick et al., "Characterization of Polyethylenimine," *Journal of Macromolecular Science—Chemistry*, vol. A4, No. 6, Oct. 1970, pp. 1301-1314.

Article—G. E. Ham, "Polymerization of Aziridines," *Polymeric Amines and Ammonium Salts*, ed. E. J. Goethals, Pergamon Press, Oxford, 1980, pp. 1-178.

Article—Helander et al., "Polyethyleneimine is an effective permeabilizer of Gram-negative bacteria," *Microbiology*, vol. 143, 1997, pp. 3193-3199.

Article—Klamann, Dieter, "Organische Stickstoff-Verbindungen mit einer C,N-Doppelbindung," Teil 1, 1990, "Methoden der Organischen Chemie," Houben-Weyl, 4 Ed., vol. E14b, published by Georg Thieme Verlag, 1963, pp. 440-4420.

Article—Kloeckner et al., "Degradable gene carriers based on oligomerized polyamines," *European Journal of Pharmaceutical Sciences*, vol. 29, 2006, pp. 414-425.

Article—Kloeckner et al., "Gene Carriers Based on Hexanediol Diacrylate Linked Oligoethyleneimine: Effect of Chemical Structure of Polymer on Biological Properties," *Bioconjugate Chem.*, vol. 17, 2006, pp. 1339-1345.

Article—Lukovkin et al., "NMR $^{13}$C Study of the Structure of Polyethyleneimine," *European Polymer Journal*, vol. 9, 1973, pp. 559-565.

Article—Peng et al., "Investigation of the degradation mechanism of cross-linked polyethyleneimine by NMR spectroscopy," *Polymer Degradation and Stability*, vol. 93, 2008, pp. 476-482.

Article—Saegusa et al., "Linear Polyalkylenimines," *Polymeric Amines and Ammonium Salts*, ed. E. J. Goethals, Pergamon Press, Oxford, 1980, pp. 55-66.

Article—St. Pierre et al., "Carbon-13 NMR Analysis of Polyethyleneimine," *Polymer. Prepr.*, vol. 22, 1981, pp. 128-129.

Article—St. Pierre et al., "$^{13}$C-NMR Analysis of Branched Polyethyleneimine," *J. Macromol. Sci.-Chem.*, vol. A22(5-7), 1985, pp. 877-887.

Article—Schultz, Rolf Christian, "Polymere mit Heteroatomen in der Polymer-Hauptkette," *Makromolekulare Stoffe*, Herbert Bartl, "Methoden der Organischen Chemie," Houben-Weyl, 4. Ed., vol. E 20, published by Georg Thieme Verlag, 1987, pp. 1367-1379.

Article—Tanaka et al., "High Molecular Weight Linear Poly(ethylenimine) and Poly(N-methylethylenimine)," *Macromolecules*, vol. 16, No. 6, 1983, pp. 849-853.

Article—Tarcha et al., "Synthesis and characterization of chemically condensed oligoethylenimine containing beta-aminopropionamide linkages for siRNA delivery," *Biomaterials*, vol. 28, 2007, pp. 3731-3740.

Article—von Harpe et al., "Characterization of commercially available and synthesized polyethylenimines for gene delivery," *Journal of Controlled Release*, vol. 69, 2000, pp. 309-322.

Article—Weyts et al., "New synthesis of linear polyethyleneimine," *Polymer Bulletin*, vol. 19, 1988, pp. 13-19.

Article—Zintchenko et al., "Simple Modifications of Branched PEI Lead to Highly Efficient siRNA Carriers with Low Toxicity," *Bioconjugate Chem.*, vol. 19, 2008, pp. 1448-1455.

Material Safety Data Sheet for Virex II 128 from Diversey, Inc. dated May 14, 2010, 4 pages.

ASTM E2315-03 (Reapproved 2008)—Standard Guide for Assessment of Antimicrobial Activity Using a Time-Kill Procedure, Apr. 1, 2008, Originally approved in 2003, 5 pages.

Product Information on Lupasol® (Polyethylenimines for creative connections) from BASF, 10 pages.

Technical Information for HM Polymin® from BASF dated Apr. 2008, 8 pages.

Technical Information for Polymin® SK from BASF dated Jul. 2005, 8 pages.

Thesis by Michael J. Simons entitled Hydrophobically Modified Polyethyleneimines and Ethoxylated Polyethyleneimines, 2007, 71 pages.

* cited by examiner

WIPE FOR USE WITH A GERMICIDAL SOLUTION

BACKGROUND OF THE INVENTION

Wipes have been treated with antimicrobial agents for cleaning a wide variety of different surfaces, including hard surfaces, skin, etc. One class of antimicrobial agents that has been employed are water soluble or dispersible cationic antimicrobial actives, such as quaternary ammonium compounds (e.g., benzethonium or benzalkonium salts). These antimicrobial agents can be incorporated into an aqueous germicidal solution that is applied to the wipe during manufacturing (i.e., pre-moistened wipe) or subsequently added to the wipe by the consumer just prior to use. One problem, however, is that certain antimicrobial agents can become bound to the polar fibers and are thus generally less effective in killing bacteria present on a surface. Another problem is that the antimicrobial agent becomes readily exhausted after a short period of time such that they only mildly inhibit growth or may only be used for a very limited number of wipes. One attempt to solve this problem is described in U.S. Pat. No. 5,421,898. In the '898 patent, the release of disinfectants from a substrate is controlled by coating the substrate with a residue of an aqueous composition of a water soluble polymer and a quaternary disinfectant. The water soluble polymer (e.g., polyvinyl alcohol) has a weight average molecular weight of 85,000 to 186,000 and a degree of hydrolysis of 87% to 89%. Unfortunately, however, coatings of this nature are still not effective enough in inhibiting the absorption of the quaternary disinfectants on polar materials, such as cellulosic-based fibrous webs. Furthermore, such polymer coatings can also reduce antimicrobial efficacy by leaching out of the wipe during use and blocking the cell walls of the bacteria from the antimicrobial agent.

As such, a need currently exists for an antimicrobial wipe that is effective and able to release a substantial portion of the antimicrobial agent during use.

SUMMARY OF THE INVENTION

In accordance with one embodiment of the present invention, a wipe for use with a germicidal solution is disclosed. The wipe comprises a fibrous substrate on which is disposed a polymer coating that contains a release agent and a cell permeabilizer. The release agent includes a crosslinked polyamideamine and the cell permeabilizer includes a polycationic substance. The crosslinked polyamideamine has a weight average molecular weight of about 500,000 grams per mole or more, and the ratio of the weight average molecular weight of the crosslinked polyamideamine to the weight average molecular weight of the polycationic substance is greater than 1.

In accordance with another embodiment of the present invention, a method for disinfecting a surface is disclosed. The method comprises contacting the surface with a wipe impregnated with a germicidal solution so that the solution is expressed therefrom. The germicidal solution comprises an antimicrobial agent. The wipe comprises a fibrous substrate on which is disposed a polymer coating that contains a release agent and a cell permeabilizer. The release agent includes a crosslinked polyamideamine and the cell permeabilizer includes a polycationic substance, wherein the crosslinked polyamideamine has a weight average molecular weight of about 500,000 grams per mole or more, and the ratio of the weight average molecular weight of the crosslinked polyamideamine to the weight average molecular weight of the polycationic substance is greater than 1.

Other features and aspects of the present invention are set forth in greater detail below.

DETAILED DESCRIPTION OF REPRESENTATIVE EMBODIMENTS

Definitions

As used herein the term "nonwoven web" generally refers to a web having a structure of individual fibers or threads which are interlaid, but not in an identifiable manner as in a knitted fabric. Examples of suitable nonwoven webs include, but are not limited to, meltblown webs, spunbond webs, carded webs, wetlaid webs, airlaid webs, etc. The basis weight of the nonwoven web may vary, such as from about 5 grams per square meter ("gsm") to 120 gsm, in some embodiments from about 10 gsm to about 70 gsm, and in some embodiments, from about 15 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, at al. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers are generally not tacky when they are deposited onto a collecting surface. Spunbond fibers may sometimes have diameters less than about 40 microns, and are often from about 5 to about 20 microns.

As used herein, the term "carded web" refers to a web made from staple fibers that are sent through a combing or carding unit, which separates or breaks apart and aligns the staple fibers in the machine direction to form a generally machine direction-oriented fibrous nonwoven web. Such fibers are usually obtained in bales and placed in an opener/blender or picker, which separates the fibers prior to the carding unit. Once formed, the web may then be bonded by one or more known methods.

As used herein, the term "airlaid web" refers to a web made from bundles of fibers having typical lengths ranging from about 3 to about 19 millimeters (mm). The fibers are separated, entrained in an air supply, and then deposited onto a forming surface, usually with the assistance of a vacuum supply. Once formed, the web is then bonded by one or more known methods.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to an antimicrobial wipe that contains a polymer coating having a synergistic combination of ingredients for providing controlled release of an antimicrobial agent and also good antimicrobial efficacy. One such ingredient is a high molecular weight polyamideamine release agent. Due to the polycationic nature of the release agent, it is able to adhere to the wipe, which is generally formed from fibers having a negative surface charge (e.g., cellulosic fibers). In this manner, the release agent can occupy binding sites on the wipe to inhibit the antimicrobial agent from adhering thereto, thus allowing it to be expressed in the germicidal solution to kill microbes on the desired surface. The adherence of the release agent to the wipe is even further enhanced by crosslinking the polyamideamine to increase its molecular weight, thereby enable it to form a structural network that physically adheres to the wipe and that can block the antimicrobial agent from binding thereto. Furthermore, the polyamideamine is amidated so that it contains secondary and/or tertiary amides. Without intending to be limited by theory, it is believed that such amidation can help render the coating amphiphilic, thus making it is less soluble in an aqueous germicidal solution and more likely to remain on the wipe during use. While the polyamideamine is able to adhere to the wipe and help block the antimicrobial agent from binding thereto, it is sometimes possible for a small amount to leach out into the germicidal solution. Due to the relatively large size of the crosslinked network, any expressed polyamideamine could potentially restrict access of the antimicrobial agent to the cell walls of bacteria. In this regard, a cell permeabilizer is also employed in the polymer coating to enhance the efficacy of the antimicrobial agent during use. More particularly, polycationic materials are particularly useful in permeabilizing the outer cell membrane without adversely impacting the ability of the polyamideamine to release the antimicrobial agent within the wipe.

Various embodiments of the present invention will now be described in more detail.

I. Polymer Coating

As indicated, the polymer coating of the present invention contains a polyamideamine release agent. Such polymers are generally formed from a polyamine prepolymer that is reacted with a crosslinking agent to form a branched crosslinked network having a variety of different possible shapes, such as hyperbranched, dendritic, comb-like, and so forth. The prepolymer may be a polyalkylenepolyamine that contains 3 or more basic nitrogen atoms, and in some embodiments, from 3 to 10 basic nitrogen atoms in the molecule. Examples of suitable polyalkylenepolyamines include, for instance, diethylenetriamine, triethylenetetramine, tetraethylenepentamine, pentaethylenehexamine, diaminopropyleneethylenediamine, trisaminopropylamine, polyethyleneimine, etc., as well as mixtures thereof. In one embodiment, for example, the polyamine is prepared by polymerizing ethyleneimine in the presence of a catalyst (e.g., carbon dioxide, sodium bisulfite, sulfuric acid, hydrogen peroxide, hydrochloric acid, acetic acid etc). The starting polyethyleneimine may have a weight average molecular weight of from about 300 to about 1,000,000, and in some embodiments, from about 10,000 to about 75,000. The prepolymer may also be a polyamine that is grafted with ethyleneimine, such as described in U.S. Pat. No. 4,144,123 to Scharf, et al., which is incorporated herein in its entirety by reference thereto for all relevant purposes. This may be accomplished, for example, by allowing ethyleneimine to act on the polyamine in the presence of acids (e.g., sulfuric acid, phosphoric acid, boron trifluoride etherates, etc.). For example, from 1 to 50, and in some embodiments, from 2 to 25 ethyleneimine units may be grafted per basic nitrogen group in the polyamine. Other methods for preparing polyamines are well known in the art and described, for instance, in U.S. Pat. No. 2,182,306 to Ulrich et al.; U.S. Pat. No. 3,033,746 to Mayle et al.; U.S. Pat. No. 2,208,095 to Esselmann et al.; U.S. Pat. No. 2,806,839 to Crowther; and U.S. Pat. No. 2,553,696 to Wilson.

Amidation of the polyamine may be accomplished in a variety of different ways. For example, amidation of the prepolymer (not crosslinked) may occur through condensation of a carboxylic acid with primary or secondary amine groups of the polyamine. Likewise, crosslinking of an amidated prepolymer and/or unamidated prepolymer may also lead to amidation. In one embodiment, for example, an amidated polyamine prepolymer is initially prepared by a condensation reaction of polyalkylenepolyamine with a mono- or multifunctional carboxylic acid or derivative thereof (e.g., carboxylic esters, carboxylic anhydrides, carbonyl halides, or alkyldiketenes) that contains from 1 to 28 carbon atoms, and in some embodiments from 1 to 18, carbon atoms, and which may be saturated or may contain one or more ethylenically unsaturated nonconjugated double bonds. Suitable monofunctional carboxylic acids may include, for instance, formic acid, acetic acid, propionic acid, butyric acid, capric acid, 2-ethylhexanoic acid, benzoic acid, lauric acid, myristic acid, palmitic acid, stearic acid, oleic acid, linoleic acid, arachidic acid, erucic acid, behenic acid, as well as derivatives and mixtures thereof. Suitable multi-functional carboxylic acids likewise include dicarboxylic acids, such as succinic acid, maleic acid, adipic acid, glutaric acid, suberic acid, sebacic acid, terephthalic acid, etc.; tricarboxylic acids; polycarboxylic acids, as well as derivatives and mixtures thereof. Fatty acid mixtures may, for example, also be employed that are obtained from naturally occurring fatty esters, such as from coconut fat, tallow, soybean oil, linseed oil, rapeseed soil and fish oil. Half-esters of dicarboxylic acids, such as monomethyl succinate, monoethyl succinate, monomethyl maleate, monomethyl fumarate and mono-tert-butyl maleate, and monoethylenically unsaturated carboxylic acids, such as acrylic acid and methacrylic acid, are also suitable.

As a result of amidation, at least a portion of the primary and secondary nitrogen atoms in the polyalkylenepolyamine form secondary and tertiary amides, respectively. Typically, from about 0.1% to about 90% of the nitrogen atoms capable of undergoing amidation in the polyalkylenepolyamine are present as amido groups so that the polymer retains at least some NH groups for subsequent reaction, such as with a crosslinking agent. If desired, the polymer may only be "partially" amidated in that the polyalkylenepolyamine undergoes only from about 1% to about 50%, and in some embodiments, from about 2% to about 30% amidation. Such partially amidated condensates are described, for instance, in U.S. Pat. No. 5,536,370 to Scherr, et al., which is incorporated herein in its entirety by reference thereto for all relevant purposes.

Crosslinking of the prepolymer (amidated or unamidated) may occur using any of a variety of different crosslinking agents as is known in the art. Typically, crosslinking agents containing at least two functional groups are employed, such as bischlorohydrin or glycidyl ethers, dichloropolyalkylene glycols, dichloroalkanes or vicinal dichloroalkanes (e.g., 1,2-dichloroethane, 1,2-dichloropropane, 1,3-dichloropropane, 1,4-dichlorobutane and 1,6-dichlorohexane), epichlorohydrin reaction products (e.g., glycerol, ethoxylated or propoxylated glycerols, polyglycerols having from 2 to 15 glycerol units in the molecule and polyglycerols which may be ethoxylated and/or propoxylated are used as polyhydric alcohols). Halogen-free crosslinking agents may also be employed. Such halogen-free crosslinking agents are typically polyfunctional (e.g., bifunctional) and include, for instance, (1) ethylene carbonate, propylene carbonate and/or urea, (2) monoethylenically unsaturated carboxylic acids and esters, amides and anhydrides thereof, at least dibasic saturated carboxylic acids or polycarboxylic acids and the esters, amides and anhydrides derived from each of them, such as described above, (3) reaction products of polyetherdiamines, alkylenediamines, polyalkylenepolyamines, alkylene glycols, polyalkylene glycols or mixtures thereof with monoethylenically unsaturated carboxylic acids, esters, amides or anhydrides of monoethylenically unsaturated carboxylic acids, the reaction products having at least two ethylenically unsaturated double bonds, and carboxamido, carboxyl or ester groups as functional groups, (4) reaction products of dicarboxylic esters with ethyleneimine, which reaction products contain at least two aziridino groups, and mixtures of the stated crosslinking agents, etc. Such crosslinking agents are described in more detail in U.S. Pat. No. 6,056,967 to Steuerle, et al., which is incorporated herein in its entirety by reference thereto for all relevant purposes. Multi-functional carboxylic acids and derivatives thereof, such as described above, are particularly suitable crosslinking agents. In addition to increasing molecular weight, crosslinking with certain types of agents (e.g., multi-functional carboxylic acids) may also result in amidation of the polymer.

In addition to the modifications referenced above, it should also be understood that the polyamideamine may be modified using various other techniques known in the art. For example, the polyamideamine may be alkoxylated—before, after, and/or during amidation and/or crosslinking. The term "alkoxylation" generally refers to the reaction of an amines with an alkylene oxide. Suitable alkylene oxides include, for instance, ethylene oxide, propylene oxide, isobutylene oxide, 1,2-butylene oxide, 2,3-butylene oxide, pentylene oxide, styrene oxide, as well as mixtures thereof. The ratio of alkylene oxide groups to acidic hydrogen atoms bound to nitrogen in the amine is typically from about 1:1 to about 300:1. Techniques for reacting an alkylene oxide with a polyamine are known in the art, and described in more detail in U.S. Pat. No. 6,235,940 to Mohr, et al. and U.S. Pat. No. 7,736,525 to Thankashan, et al., which are incorporated herein in their entirety by reference thereto for all purposes. For example, in certain embodiments, the reaction is carried out in the presence of a basic catalyst, such as alkali metal hydroxides (e.g., lithium hydroxide, sodium hydroxide, potassium hydroxide or cesium hydroxide), alkali metal alkoxides (e.g., sodium or potassium methoxide, potassium ethoxide, potassium isopropoxide or potassium tert-butoxide), etc.

Regardless of the particular manner in which it is formed, the resulting crosslinked polyamidoamine has a relatively high average molecular weight. That is, the weight average molecular weight is typically about 500,000 grams per mole or more, in some embodiments about 750,000 grams per mole or more, and in some embodiments, from about 1,000,000 to about 2,000,000 grams per mole, determined using any known technique, such as by light scattering. Such high molecular weight structures are believed to facilitate the ability of the polymer network to become structurally integrated with the fibrous substrate, thus enhancing its ability to block the antimicrobial agent from adhering to the fibrous substrate.

As indicated above, however, the relatively large size of the crosslinked polyamidoamine network may cause blockage of bacteria cell walls if any is leached out of the wipe during use. In this regard, the present inventors have discovered that a polycationic substance may also be employed in the polymer coating to help permeabilize the cell walls of the bacteria and increase the efficacy of the antimicrobial agent, thereby offsetting any reduction in efficacy that might have been encountered due to the leaching of the release agent. For example, the outer leaflet of the membrane of Gram-negative bacteria possesses unique liposaccharide ("LPS") molecules that often contribute to the formation of a permeability barrier against hydrophobic substances and macromolecules. Without intending to be limited by theory, it is believed that the polycationic substance can intercalate onto the outer membrane, causing it to weaken and become more susceptible to attack by the antimicrobial agent.

Generally speaking, the polycationic substance is a polymer having a molecular weight that is low enough so that it does not block the bacteria cells in the manner described above, but also high enough so that it does not adversely impact the extent to which the polymer coating is able to bind to the wipe. For example, the polycationic substance typically has a lower average molecular weight than the polyamideamine release agent such that the ratio of the average molecular weight of the release agent to the average molecular weight of the permeabilizer is greater than about 1, in some embodiments from about 1.1 to about 3, and in some embodiments, from about 1.2 to about 1.8. The weight average molecular weight of the polycationic cell permeabilizer may, for instance, be from about 200,000 grams per mole to about 1,500,000 grams per mole, in some embodiments from about 400,000 grams per mole to about 1,200,000 grams per mole, and in some embodiments, from about 600,000 to about 1,000,000 grams per mole, determined using any known technique, such as by light scattering.

Suitable polycationic substances for use as a cell permeabilizer may include, for instance, polymyxin, polylysine, protamine, polyamines, etc., as well as derivatives and mixtures thereof. In one particular embodiment, the polyamine may be a crosslinked polyamideamine such as described above. Among other things, the present inventors have discovered that the use of a crosslinked polyamideamine can possess at least some of the same benefits as the release agent, but can effectively function as a permeabilizer due to its lower molecular weight. In fact, in certain embodiments, the cell permeabilizer may actually be derived from a starting material that is similar to the high molecular weight polyamideamine described above. This may be accomplished by subjecting the starting material to a filtration process (e.g., ultrafiltration) that removes a low molecular weight fraction as permeate and isolates a high molecular weight fraction. The high molecular weight fraction may serve as the permeabilizer, which has a molecular weight lower than the starting material and within the ranges noted above. Although not required, the high molecular weight fraction used for the cell permeabilizer may have a narrower molecular weight distribution than the starting material. For example, the initial starting material may have a polydispersity index (weight average molecular weight divided by the number average molecular weight) of about 400 or more, such as determined using conventional techniques (e.g., gel permeation chromatography). The high molecular weight fraction employed as the cell permeabilizer may, however, have a polydispersity index of from 2 to 350, and in some embodiments, from about 10 to 300. Various filtration techniques and materials used for such separate such polymers are described, for instance, in U.S. Pat. No. 6,056,967 to Steuerle, et al.

The relative amounts of the polycationic cell permeabilizer and the polyamideamine release agent may vary. In most embodiments, however, it is desired that the cell permeabilizer constitutes a greater weight percentage of the polymer coating to ensure sufficient antimicrobial efficacy. For instance, the weight ratio of the cell permeabilizer to the release agent is typically from about 1 to about 20, in some embodiments from about 1.5 to about 15, and in some embodiments, from about 2 to about 10. The cell permeabilizer may, for instance, constitute from about 50 wt. % to about 99 wt. %, in some embodiments from about 60 wt% to about 95 wt. %, and in some embodiments, from about 70 wt. % to about 90 wt. % of the coating, on a dry basis. Likewise, the release agent may constitute from about 1 wt. % to about 50 wt. %, in some embodiments from about 5 wt. % to about 40 wt. %, and in some embodiments, from about 10 wt. % to about 30 wt. % of the coating, on a dry basis.

II. Wipe Construction

The wipe of the present invention generally contains a fibrous substrate on which the polymer coating is disposed. The polymer coating may be applied to the substrate during its formation or simply applied onto all or a portion of a surface of the wipe using known techniques, such as printing, dipping, spraying, melt extruding, coating (e.g., solvent coating, powder coating, brush coating, etc.), foaming, and so forth. In one embodiment, for example, the coating is applied to the wipe by dipping, spraying, or printing. The coating may be continuous or discontinuous over the surface of the wipe. The pattern may, for example, cover only from about 5% to about 95%, in some embodiments from about 10% to about 90%, and in some embodiments, from about 20% to about 75% of a surface of the wipe. Such patterned application may have various benefits, including enhanced softness and drape, improved absorbency, etc.

The ingredients of the polymer coating are typically incorporated into a coating solution prior to being applied to the fibrous substrate. The manner in which the solution is formed may vary as is known to those skilled in the art. In one embodiment, for example, the polyamideamine release agent and the polycationic cell permeabilizer may be combined together with a solvent to form a single coating solution that is applied to the substrate. Alternatively, the release agent and cell permeabilizer may be applied in separate coating steps so that they are present in different layers of a single coating. The solvent(s) used to form the coating formulation may vary, such as water, organic solvents, etc. Because the polyamideamine and polycationic cell permeabilizer are generally water soluble, water is often employed. If desired, the substrate may be dried at a certain temperature after each coating step to drive the solvents from the solution. Drying may be accomplished using any known technique, such as an oven, drying rolls (e.g., through-air drying, Yankee dryer), etc. The temperature at which the wipe is dried generally depending on the time period over which it is dried, but is typically at least about 20° C., and in some embodiments, from about 30° C. to about 100° C.

The solids add-on level of the coating is typically from about 0.1% to about 20%, in some embodiments from about 0.5% to about 15%, and in some embodiments, from about 1% to about 10%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum functionality of the substrate, while higher add-on levels may provide optimum efficacy.

The nature of the fibrous substrate may vary depending on the intended use, and may include materials such as nonwoven webs, knitted fabrics, woven fabrics, cotton fabrics, etc. In one embodiment, for example, the fibrous substrate includes a nonwoven web that contains an absorbent material of sufficient wet strength and absorbency for use in the desired application. For example, the nonwoven web may include absorbent cellulosic fibers formed by a variety of pulping processes, such as kraft pulp, sulfite pulp, thermomechanical pulp, etc. Such pulp fibers may be high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability. Further, other absorbent fibers that may be used in the present invention, such as abaca, sabai grass, milkweed floss, pineapple leaf, cellulosic esters, cellulosic ethers, cellulosic nitrates, cellulosic acetates, cellulosic acetate butyrates, ethyl cellulose, regenerated celluloses (e.g., viscose or rayon), and so forth.

Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al.

When employed, the synthetic fibers may be monocomponent or multicomponent. Multicomponent fibers are fibers that have been formed from at least two polymer components. Such fibers are usually extruded from separate extruders but spun together to form one fiber. The polymers of the respective components are usually different from each other although multicomponent fibers may include separate components of similar or identical polymeric materials. The individual components are typically arranged in substantially constantly positioned distinct zones across the cross-section of the fiber and extend substantially along the entire length of the fiber. The configuration of such fibers may be, for example, a side-by-side arrangement, a pie arrangement, or any other arrangement. Multicomponent fibers and methods of making the same are taught in U.S. Pat. No. 5,108,820 to Kaneko, et al., U.S. Pat. No. 4,795,668 to Kruege, et al., U.S. Pat. No. 5,162,074 to Hills, U.S. Pat. No. 5,277,976 to Hogle, et al., U.S. Pat. No. 5,336,552 to Strack, et al., U.S. Pat. No. 5,466,410 to Hills, U.S. Pat. No. 5,069,970 to Largman, et al., U.S. Pat. No. 5,057,368 to Largman, et al., U.S. Pat. No. 5,382,400 to Pike, et al., and U.S. Pat. No. 5,989,004 to Cook. When utilized, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al.

If desired, the nonwoven web material may be a composite that contains a combination of synthetic thermoplastic polymer fibers and absorbent fibers, such as polypropylene and pulp fibers. The relative percentages of such fibers may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % synthetic polymeric fibers. The nonwoven composite may likewise contain from about 40 wt. % to about 99 wt. %, in some embodiments from 50 wt. % to about 95 wt. %, and in some embodiments, from about 60 wt. % to about 90 wt. % absorbent fibers.

Nonwoven composites may be formed using a variety of known techniques. For example, the nonwoven composite may be a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, at al.; which are incorporated herein in their entirety by reference thereto for all relevant purposes.

Alternatively, the nonwoven composite may be formed be formed by hydraulically entangling fibers and/or filaments with high-pressure jet streams of water. Hydraulically entangled nonwoven composites of staple length fibers and continuous filaments are disclosed, for example, in U.S. Pat. No. 3,494,821 to Evans and U.S. Pat. No. 4,144,370 to Boulton, which are incorporated herein in their entirety by reference thereto for all purposes. Hydraulically entangled nonwoven composites of a continuous filament nonwoven web and pulp fibers are disclosed, for example, in U.S. Pat. No. 5,284,703 to Everhart, et al. and U.S. Pat. No. 6,315,864 to Anderson, at al., which are incorporated herein in their entirety by reference thereto for all purposes.

Regardless of the materials or processes utilized to form the wipe, it is typically desired that the basis weight of the wipe be from about 20 to about 500 grams per square meter (gsm), and in some embodiments, from about 35 to about 350 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al.

III. Germicidal Solution

To impart the desired antimicrobial properties, a germicidal solution is also applied to the polymer-coated wipe. The solution may be applied to the wipe during manufacturing so that the wipe is "premoistened" prior to or during use. Alternatively, the wipe may be supplied as a "dry" wipe, and the germicidal solution can simply be added thereto by a consumer, user, etc., prior to or during use.

The wipe may be applied with a germicidal solution by any suitable method known in the art, such as spraying, dipping, saturating, impregnating, brush coating and so forth. The amount of the germicidal solution that may be added to the wipe may vary depending upon the type of wipe material utilized, the type of container used to store the wipes, the nature of the germicidal solution, and the desired end use of the wipes. Generally, each wipe contains from about 150 wt. % to about 600 wt. % and desirably from about 300 wt. % to about 500 wt. % of the germicidal solution based on the dry weight of the wipe. In embodiments in which the wipe is made from a relatively absorbent substrate (e.g., fabrics containing pulp fibers), the amount of the germicidal solution contained within the wipe can be from about 300 wt. % to about 600 wt. % and desirably about 500 wt. % based on the dry weight of the wipe. In embodiments in which the wipe is made from a relatively non-absorbent substrate (e.g., polypropylene meltblown or spunbonded fabric), the amount of the germicidal solution contained within the wipe can be from about 150 wt. % to about 500 wt. % and desirably about 400 wt. % based on the dry weight of the wipe.

Regardless of the manner in which it is applied, however, the germicidal solution generally includes an antimicrobial agent. Any antimicrobial agent that is capable of killing and/or inhibiting the growth of microorganisms (e.g., gram negative and/or positive bacteria) can be utilized in the present invention. In one particular embodiment, the antimicrobial agent includes at least one quaternary ammonium compound having the following formula:

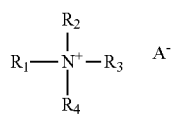

wherein, $R_1$, $R_2$, $R_3$, and $R_4$ are independently selected from the group consisting of H, $C_1$-$C_{30}$ alkyl, $C_1$-$C_{30}$ alkenyl, $C_1$-$C_{30}$ alkylethoxy, $C_1$-$C_{30}$ alkylphenolethoxy, etc.; and A is selected from the group consisting of halogens (e.g., chlorine, bromine, fluorine, etc.); methosulfates, phosphates, etc. For instance, some suitable quaternary ammonium compounds that may be used in present invention include, but are not limited to, benzalkonium chloride (BZK) or other benzalkonium halides, benzethonium chloride or other benzethonium halides, cetylpyridinium chloride, dequalinium chloride, N-myristyl-N-methyl-morpholinium methyl sulfate, poly-N-3-(dimethylammonio)propyl-N-3-(ethyleneoxyethelene dimethylammonio)propylurea dichloride, alpha-4-1-tris(2-hydroxyethyl)ammo-nium chloride-2-butenyl-omega-tris(2-hydroxyethyl)ammonium chloride, polyoxyethylene (dimethyliminio)ethylene(dimethyliminio)-ethylene dichloride.

In some embodiments, quaternary ammonium halide compounds having the following formula may be employed:

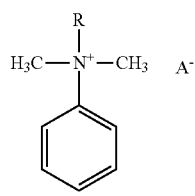

wherein,

R is a $C_8$-$C_{18}$ alkyl group; and

A is a halogen atom, such as chlorine, bromine, fluorine, etc. One commercially available example of an antimicrobial agent that includes such a quaternary ammonium compound is available under the trade name BARDAC® 208M from Lonza, Inc., Allendale, N.J. Specifically, BARDAC® 208M contains a blend of alkyl dimethyl benzyl ammonium chlorides. Other commercially available examples of suitable quaternary ammonium compounds are believed to include BARDAC® 2050 and BARDAC® 2080 (based on dialkyl ($C_8$-$C_{10}$)dimethyl ammonium chloride); BARDAC® 2250 and BARDAC® 2280 (didecyl dimethyl ammonium chloride); BARDAC® LF and BARDAC® LF 80 (based on dioctyl dimethyl ammonium chloride); BARQUAT® MB-50 and BARQUAT® MB-80 (based on alkyl dimethyl benzyl ammonium chloride); BARQUAT® MX-50 and BARQUAT® MX-80 (based on alkyl dimethyl benzyl ammonium chloride); BARQUAT® OJ-50 and BARQUAT® OJ-80 (based on alkyl dimethyl benzyl ammonium chloride); BARQUAT® 4250, BARQUAT® 4280, BARQUAT® 4250Z, and BARQUAT® 4280Z (based on alkyl dimethyl benzyl ammonium chloride and/or alkyl dimethyl ethyl benzyl ammonium chloride); and BARQUAT® MS-100 (based on myristyl dimethyl benzyl ammonium chloride), which are available from Lonza, Inc. Suitable germicidal solutions containing such compounds are also commercially available, such as VIREX® II 128, which is sold by Diversey, Inc. and contains N-alkyl dimethyl benzyl ammonium chloride, didecyl dimethyl ammonium chloride, and ethanol. Still other solutions of blended quaternary ammonium compounds are available from Ecolab, Inc. of St. Paul, Minn. under the trade designation OASIS™ (e.g., OASIS™ 146).

In addition to quaternary ammonium compounds, other antimicrobial agents may also be utilized in the present invention. For instance, some suitable antimicrobial agents that may be utilized include, but are not limited to, alcohols, halogenated diphenyl ethers like 2,4,4'-trichloro-2'-hydroxy-diphenyl ether (Triclosan® or TCS) or 2,2'-dihydroxy-5,5'-dibromo-diphenyl ether; phenolic compounds like phenoxyethanol, phenoxy propanol, phenoxyisopropanol, para-chloro-meta-xylenol (PCMX), etc.; bisphenolic compounds, such as 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl)sulphide, and bis(2-hydroxy-5-chlorobenzy-l)sulphide; halogenated carbanilides (e.g., 3,4,4'-trichlorocarbanilides (Triclocarban® or TOG); benzyl alcohols; chlorhexidine; chlorhexidine gluconate; and chlorhexidine hydrochloride. Other suitable antimicrobial agents are described in WO 96/06152; WO 96106153; and U.S. Pat. No. 6,201,695 to Beerse, et al. In addition, various other antimicrobial agents are set forth in Title 21, Section 178.010 of the United States Code of Federal Regulations (C.F.R.).

The amount of the antimicrobial agent utilized in the germicidal solution can generally vary depending on the relative amounts of the other components present within the solution. Typically, the antimicrobial agent is present in the solution in an amount from about 0.01% to about 20% by weight, in some embodiments from about 0.1% to about 15% by weight, and in some embodiments, from about 0.2% to about 10% by weight of the germicidal solution.

It is usually desired that an aqueous solvent (e.g., water) is employed as the carrier of the germicidal solution, although it should be understood that other suitable carriers are also contemplated in the present invention. For example, water is typically present in the germicidal solution in an amount from about 10 wt. % to about 99 wt. %, in some embodiments from about 40 wt. % to about 95 wt. %, and in some embodiments, from about 60 wt. % to about 94 wt. % of the germicidal solution.

In some instances, the germicidal solution of the present invention may also include one or more non-aqueous solvents. Although not required, non-aqueous solvents can sometimes aid in dissolving certain components (e.g., antimicrobial agent) of the germicidal solution. Moreover, in some instances, the non-aqueous solvent may also enhance the antimicrobial efficacy of the germicidal solution.

Examples of some suitable non-aqueous solvents include, but are not limited to, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Especially desired solvent combinations include a glycol, particularly hexylene and/or propylene glycol, and one or more lower alcohols, particularly isopropanol, n-propanol, and/or ethanol. The amount of non-aqueous solvents utilized in the germicidal solution can generally vary depending on the relative amounts of the other components present within the solution. When utilized, non-aqueous solvents are typically present in the solution in an amount from about 0.001% to about 30% by weight, in some embodiments from about 0,1 to about 15% by weight, and in some embodiments, from about 1% to about 15% by weight of the germicidal solution.

The germicidal solution may optionally include additional ingredients to impart various benefits. For instance, the germicidal solution may also employ surfactants to enhance the wettability of the composition on a substrate, to help emulsify or dissolve other ingredients, to increase viscosity, etc. When utilized, the amount of the surfactants utilized in the germicidal solution may generally vary depending on the relative amounts of the other components present within the composition. The surfactants may include nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Ionic surfactants (i.e., anionic, cationic, or amphoteric surfactants) may also be employed in the germicidal solution. For instance, one class of amphoteric surfactants that may be used are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine. Additional classes of amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryidimethylcarboxymethylbetaine, lauryldimethylcarboxyethylbetaine, cetyldimethylcarboxymethylbetaine, lauryl-bis-(2-hydroxyethyl)-carboxymethylbetaine, oleyldimethylgammacarboxypropylbetaine, lauryl-bis-(2-hydroxypropyl)-carboxyethylbetaine, cocoamidodimethylpropylsultaine, stearylamidod imethyl propylsultaine, laurylamido-bis-(2-hydroxyethyl)-propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Moreover, exemplary anionic surfactants include alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkyl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof. Particular examples of anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group may be straight chain (e.g., lauryl) or branched (e.g., 2-ethylhexyl). The cation of the anionic surfactant may be an alkali metal (e.g., sodium or potassium), ammonium, $C_1$-$C_4$ alkylammonium (e.g., mono-, di-, tri-), or $C_1$-$C_3$ alkanolammonium (e.g., mono-, di-, tri). More specifically, such anionic surfactants may include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

The germicidal solution may also contain a preservative or preservative system to inhibit the growth of microorganisms over an extended period of time. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from Mcintyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J.

The pH of the germicidal solution may also be controlled within a range that is considered more biocompatible. For instance, it is typically desired that the pH is within a range of from about 5 to about 8, and in some embodiments, from about 6 to about 7. Various pH modifiers may be utilized in the germicidal solution to achieve the desired pH level. Some examples of pH modifiers that may be used in the present invention include, but are not limited to, mineral acids, sulfonic acids (e.g., 2-[N-morpholino]ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. When utilized, the pH modifier may be present in any effective amount needed to achieve the desired pH level.

To better enhance the benefits to consumers, other optional ingredients may also be used. For instance, some classes of ingredients that may be used include, but are not limited to: antioxidants (product integrity); anti-reddening agents, such as aloe extract; astringents--cosmetic (induce a tightening or tingling sensation on skin); colorants (impart color to the product); deodorants (reduce or eliminate unpleasant odor and protect against the formation of malodor on body surfaces); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and thickeners (to increase the viscosity of the composition).

Prior to use, the wipe is contacted with a sufficient amount of germicidal solution to disinfectant or sanitize a surface. As the wipe is rubbed on the surface, it releases the germicidal solution, which contacts bacteria present thereon. The wipe can also provide an abrasive action and a reabsorption capability to remove contaminants from the surface. After use, the wipe can be disposed. The germicidal solution may remain on the surface to help kill and/or inhibit the growth of bacteria thereon for a certain period of time. Although the amount of antimicrobial agent released from the wipe in the present invention may vary depending on the nature of the antimicrobial agent and/or other solution components, it is typically present in an amount less than about 2000 parts per million (ppm) of the germicidal solution released from the wipe. In some embodiments, for example, a quaternary ammonium halide antimicrobial agent, as described in more detail above, can be present in the released germicidal solution in an amount less than about 500 ppm, and in some embodiments from about 150 ppm to about 400 ppm of the released solution. Again, even when present in the released germicidal solution in such small amounts, the desired level of antimicrobial efficacy can still be achieved.

The wipe of the present invention may kill and/or inhibit (e.g., reduce by a measurable amount or to prevent entirely) the growth of one or more microorganisms when exposed thereto. Examples of microorganisms that may be inhibited include bacteria (including cyanobacteria and Mycobacteria), protozoa, algae, fungi (e.g., molds and yeast), viruses, prions, and other infectious particles. For example, the coating may inhibit the growth of several medically significant bacterial groups, such as Gram negative rods (e.g., *Entereobacteria*); Gram negative curved rods (e.g., *Heliobacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g,. *Ricckettsia* and *Chlamydia*); acid fast rods (e.g., *Myobacterium, Nocardia*, etc.); spirochetes (e.g., *Treponema, Borellia*, etc.); and mycoplasmas (i.e., bacteria that lack a cell wall). Particularly species of bacteria that may be inhibited with the composition of the present invention include *Escherichia coli* (Gram negative rod), *Klebsiella pneumonia* (Gram negative rod), *Streptococcus* (Gram positive cocci), *Salmonella choleraesuis* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

Upon exposure for a certain period of time, the wipe may provide a log reduction of at least about 2, in some embodiments at least about 3, in some embodiments at least about 4, and in some embodiments, at least about 5 (e.g., about 6). Log reduction, for example, may be determined from the % population killed by the composition according to the following correlations:

| % Reduction | Log Reduction |
| --- | --- |
| 90 | 1 |
| 99 | 2 |
| 99.9 | 3 |
| 99.99 | 4 |
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 15 minutes, in some embodiments 10 minutes, in some embodiments 5 minutes, and in some embodiments, 1 minute.

As discussed above, it has also been discovered that the selection and relative amounts of the components of the polymer coating on the wipe can allow control over the amount of antimicrobial agent absorbed into the wipe and not released during use. This phenomenon can be quantified by the antimicrobial "Release Value" according to the formula below:

$$100 \times [Q_r/Q_i]$$

wherein, $Q_i$ is the amount of antimicrobial agent added to the germicidal solution, and $Q_r$ is the amount of antimicrobial agent released as a solution released from the wipe. In most embodiments of the present invention, the "Release Value" is about 80% or more, in some embodiments about 85% or more, in some embodiments about 90% or more, and in some embodiments, from about 95% to about 99%.

The present invention may be better understood with reference to the following examples.

EXAMPLE 1

An uncoated fibrous web was tested for its quaternary amine release properties. The tested fabric was WYPALL®X70, a HYDROKNIT™ material available from Kimberly-Clark® Professional. The web had an average basis weight of 82 grams per meter squared (gsm) and contained pulp fibers hydroentangled into a polypropylene spunbond web having a basis weight of approximately 1 gsm. The quaternary amine was Oasis® 146 from ECOLAB®, Inc., and it was mixed to a 400 ppm of total quaternary amine. Oasis® 146 contains 3% of alkyl $C_{14}$ 50%, $C_{12}$ 40%, $C_{16}$ 10% dimethyl benzyl ammonium chloride, 2.25% of octyl benzyl ammonium chloride, 1.35% didecyl dimethyl ammonium chloride, 0.9% dioctyl dimethyl ammonium chloride, and q.s. water. The fabric was tested using the following procedure:

Mix 1 liter of the Oasis® 146 at 400 ppm in a large one liter beaker.
Collect initial sample of the mixed Oasis® 146 for base line concentration.
Cut 2 to 3 wipes (specimens) to an appropriate size to achieve approximately 1 gram wipe for 67 grams of solution.
Weigh both wipes and record weight.
Place both wipes into the one liter solution.
At 15 minutes, remove both wipes and squeeze excess liquid from wipes back into the beaker. Then squeeze extract from wipes into labeled vial for submission to for analytical testing.

The extracted sanitizer, as well as the initial Oasis® 146, was tested for quaternary amine concentration using High Pressure Liquid Chromatography (HPLC) under the following conditions and using the following procedures:

Preparation of Reagents and Stock Standard Solutions 0.1% Formic Acid
Add 900 ml of Milli-Q water to a 1000 ml volumetric flask. Pipet 1.0 ml of formic acid (EMD FX0440-11) to the flask and dilute to volume with Milli-Q water. Use as prepared.
0.1% Trifluoroacetic Acid (TFA)
Add 900 ml of Milli-Q water to a 1000 ml volumetric flask. Add one ampoule of TFA (J T Baker 9470-00-10×1 ml ampoules) to the flask and dilute to volume with Milli-Q water. Use as prepared.

Preparation of Stock Standard

Weigh accurately 0.14 grams of the Oasis® 146 (7.5% active) concentrated solution into a 10.0 ml volumetric flask. Dilute to volume with Mill-Q water and shake.

Calibration Standards

Calibration standard aliquots were measured with a 100 µl or a 500 µl Hamilton Gastight® #1750 syringe. Milli-Q water was added to the autosampler vials with a 1000 µl Hamilton Gastight® #1001 syringe. Aliquots of 100, 200, 300, 400, 500 and 700 µls were taken from the Oasis 146 stock standard solution and transferred to six 2 ml autosampler vials and labeled 1 to 6. The vials were diluted to 1000 µl with 900, 800, 700, 600, 500, and 300 µls of Milli-Q water, respectively, to prepare Oasis® 146 calibration standards.

Chromatographic Conditions—Quat Analysis

System: Agilent Series 1100 Quaternary HPLC
Column: Sielc Primesep B2 5µ 100 Å (2.1×100 mm) Part #B2-21.100.0510
Col Temp: 45° C.
Detector 1: PL-ELS 2100 (Evaporative Light Scattering Detector)
Evap Temp: 45° C.
Neb Temp: 35° C.
Gas Flow: 1.5 SLM nitrogen gas
Gain: 10×
Detector 2: Agilent Series 1100 Diode Array
Sig/Bandwth: 254 nm/4 nm
Ref/Bandwth: 360 nm/10 nm
Gradient: A—0.1% formic acid
   B—acetonitrile
   0 min: 70% A/30% B
   5.0 min: 40% A160% B
   5.1 min: 70% A/30% B
Flow rate: 0.8 ml/min
Injection vol: 10 µl
Elution Time: DODMAC—0.98 min
   $C_{12}$ DMBAC—1.3 min (approx.)
   ODDMAC—1.7 min
   $C_{14}$ DMBAC—2.4 min
   DDDMAC—2.7 min
   $C_{16}$ DMBAC—3.3 min The standard concentrations were corrected for their actual percentage in the quaternary amine solution. The % quaternary amine (quats) release results (i.e., Release Values) were based on the amount of expressed quats recovered relative to the prepared Oasis Control solution. For Example 1, the Quat Release Value was determined to be 58%.

EXAMPLE 2

The WYPALL®X70 sheet of Example 1 was coated with Polymin® SK (BASF) to a target add-on of 0.75% using the following "dip and squeeze" method:
Cut fibrous web samples into desired shape and size, and weigh sample.

Recorded dry sample weight.

Mix treatment bath using distilled and ionized water. Let bath come to room temperature.

Mix bath to a % active concentration to a target wet pick-up and target % by weight add-on.

Dip web/fabric sample into bath and squeeze out excess fluid by running the sample through an Atlas Laboratory Wringer. Alternatively, if the samples are small enough, they could be squeezed by hand.

Weight sample to verify targeted wet pick-up. Wet pick-up=(wet weight−dry weight/wet weight)*100.

If sample is not at target wet pick-up adjust lab wringer pressure or remake treatment bath at new wet pick-up target.

If wet pick-up is correct, hang wet fabric sample in oven and dry for 45 minutes at 90° C.

Let samples rehydrate over night and reweight sample.

Add-on level is calculated by (final weight−initial weight/initial weight)*100=% add-on.

If add-on level is not on target adjust bath and remake the sample.

Depending on the level of accuracy required, the actual data should be within 25% of the targeted add-on.

The finished wipes were soaked in a quaternary amine solution and the solution was expressed out of the wipe after 15 minutes as described in Example 1. The quaternary amine solution used was Oasis® 146 from ECOLAB® and was mixed to a 400 ppm of total quaternary amine. The expressed solution was tested for quaternary amine release using the same HPLC method as described in Example 1. The Quat Release Value was determined to be 89.8%. Furthermore, the expressed solution was tested for efficacy with gram negative bacterial using ASTM E2315-03 with *Escherichia coil* (*E. coli*) as the test organism. The percent reduction of *E. coli* after 1 minute of exposure was 99.999%.

EXAMPLE 3

A sample was formed as described in Example 2, except that the Polymin® SK had a target add-on level of 1.0% by weight. The Quat Release Value was determined to be 94.5% and the percent reduction of *E. coli* after 1 minute of exposure was 99.738%.

EXAMPLE 4

A sample was formed as described in Example 2, except that the Polymin® SK had a target add-on level of 1.5% by weight. The Quat Release Value was determined to be 96.3% and the percent reduction of *E. coli* after 1 minute of exposure was 89.458%.

EXAMPLE 5

A sample was formed as described in Example 2, except that the Polymin® SK had a target add-on level of 2.0% by weight. The Quat Release Value was determined to be 99.7% and the percent reduction of *E. coli* after 1 minute of exposure was 99.264%.

EXAMPLE 6

A sample was formed as described in Example 2, except that the Polymin® SK had a target add-on level of 3.0% by weight. For this Example, the fabric was not coated using a "hand" dip and squeeze method, but was instead coated using a continuous dip and squeeze method and subsequent inline impingement oven. The line speed was 23 feet per minute and the maximum dryer temperature was set at 360° F. The Quat Release Value was determined to be 100% and the percent reduction of *E. coli* after 1 minute of exposure was 76.58%.

EXAMPLE 7

A sample was formed as described in Example 2, except that the polymer was Polymin® P (BASF) and the target add-on level was 2.0% by weight. The Quat Release Value was determined to be 77.2% and the percent reduction of *E. coli* after 1 minute of exposure was 99.999%.

EXAMPLE 8

A sample was formed as described in Example 7, except that the target add-on level was 3.0% by weight. The Quat Release Value was determined to be 84% and the percent reduction of *E. coli* after 1 minute of exposure was 99.999%.

EXAMPLE 9

A sample was formed as described in Example 7, except that the target add-on level was 5.0% by weight. The Quat Release Value was determined to be 87% and the percent reduction of *E. coli* after 1 minute of exposure was 99.999%.

EXAMPLE 10

A sample was formed as described in Example 2, except that the coating contained a combination of Polymin® SK at a target add-on level of 0.25% by weight and Polymin® P at an add-on level of 5.0% by weight. The Quat Release Value was determined to be 91.7% and the percent reduction of *E. coli* after 1 minute of exposure was 99.999%.

EXAMPLE 11

A sample was formed as described in Example 2, except that the coating contained a combination of Polymin® SK at a target add-on level of 0.5% by weight and Polymin® P at an add-on level of 3.0% by weight. The Quat Release Value was determined to be 92.9% and the percent reduction of *E. coli* after 1 minute of exposure was 99.999%.

EXAMPLE 12

A sample was formed as described in Example 2, except that the coating contained a combination of Polymin® SK at a target add-on level of 0.5% by weight and Polymin® P at an add-on level of 2.5% by weight. The Quat Release Value was determined to be 86.9% and the percent reduction of *E. coli* after 1 minute of exposure was 99.999%.

EXAMPLE 13

A sample was formed as described in Example 2, except that the coating contained a combination of Polymin® SK at a target add-on level of 0.75% by weight and Polymin® P at an add-on level of 3.0% by weight. The Quat Release Value was determined to be 99.5% and the percent reduction of *E. coli* after 1 minute of exposure was 99.999%.

EXAMPLE 14

A sample was formed as described in Example 2, except that the coating contained a combination of Polymin® SK at a target add-on level of 0.75% by weight and Polymin® P at an add-on level of 5.0% by weight. The Quat Release Value was determined to be 92.1% and the percent reduction of *E. coli* after 1 minute of exposure was 99.999%.

EXAMPLE 15

A sample was formed as described in Example 2, except that the coating contained a combination of Polymin® SK at a target add-on level of 1.0% by weight and Polymin® P at an add-on level of 2.0% by weight. The Quat Release Value was determined to be 95.0% and the percent reduction of *E. coli* after 1 minute of exposure was 99.999%.

EXAMPLES 16-23

Solution samples were formed by mixing an Oasis® 146 sanitizing solution to 400 ppm, and thereafter adding a certain concentration of Polymin® SK (BASF), Polymin® P (BASF), poly(ethyleneimine) (Sigma-Aldrich), and/or ethylenediaminetetraacetic acid disodium salt (EDTA, Sigma-Aldrich). The poly(ethyleneimine) ("PEI") from Sigma-Aldrich (catalog #P3143) had a weight average molecular weight of 750,000 grams per mole. The samples were tested for efficacy using ASTM E2315-03 for *E. coli* as the test organism. The results are set forth in the Table below:

| Example | Oasis® 146 (ppm) | Polymin® SK (ppm) | Polymin® P (ppm) | PEI (ppm) | EDTA (ppm) | % Reduction *E. coli* after 1 minute exposure |
|---|---|---|---|---|---|---|
| 16 | 400 | 0 | 0 | 0 | 0 | 99.999% |
| 17 | 400 | 100 | 0 | 0 | 0 | 99.976% |
| 18 | 400 | 500 | 0 | 0 | 0 | 95.743% |
| 19 | 400 | 1000 | 0 | 0 | 0 | 93.999% |
| 20 | 400 | 0 | 1000 | 0 | 0 | 99.999% |
| 21 | 400 | 500 | 500 | 0 | 0 | 99.999% |
| 22 | 400 | 0 | 0 | 1000 | 0 | 99.999% |
| 23 | 400 | 1000 | 0 | 0 | 1000 | 65.387% |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wipe for use with a germicidal solution, wherein the wipe comprises a fibrous substrate impregnated with a germicidal solution containing an anti-microbial quaternary ammonium compound and further comprises a polymer coating disposed onto the fibrous substrate, the polymer coating containing a release agent and a cell permeabilizer, wherein the release agent includes a crosslinked polyamideamine and the cell permeabilizer includes a polycationic substance, wherein the crosslinked polyamideamine has a weight average molecular weight of about 1,000,000 to about 2,000,000 grams per mole and the polycationic substance has a weight average molecular weight of about 600,000 to about 1,000,000 grams per mol, and wherein the ratio of the weight average molecular weight of the crosslinked polyamideamine to the weight average molecular weight of the polycationic substance is greater than 1 to about 3.

2. The wipe of claim 1, wherein the polyamideamine is formed from a polyalkylenepolyamine prepolymer.

3. The wipe of claim 2, wherein the polyalkylenepolyamine is polyethyleneimine.

4. The wipe of claim 2, wherein the polyalkylenepolyamine is a polyamine that is grafted with ethyleneimine.

5. The wipe of claim 2, wherein the prepolymer is crosslinked with a polyfunctional crosslinking agent.

6. The wipe of claim 5, wherein the crosslinking agent includes a monoethylenically unsaturated carboxylic acid, or an ester, amide, or anhydride thereof.

7. The wipe of claim 1, wherein the polyamideamine is alkoxylated.

8. The wipe of claim 1, wherein the ratio of the weight average molecular weight of the crosslinked polyamideamine to the weight average molecular weight of the polycationic substance is from about 1.2 to about 1.8.

9. The wipe of claim 1, wherein the polycationic substance is a polyamine.

10. The wipe of claim 9, wherein the polyamine is a crosslinked polyamideamine.

11. The wipe of claim 1, wherein the weight ratio of the cell permeabilizer to the release agent is from about 2 to about 10.

12. The wipe of claim 1, wherein the cell permeabilizer constitutes from about 60 wt. % to about 95 wt. % of the coating and the release agent constitutes from about 5 wt. % to about 40 wt. % of the coating.

13. The wipe of claim 1, wherein the solids add-on level of the polymer coating is from about 0.5% to about 15%.

14. The wipe of claim 1, wherein the fibrous substrate contains absorbent fibers.

15. The wipe of claim 14, wherein the absorbent fibers include cellulosic fibers.

16. The wipe of claim 15, wherein the cellulosic fibers include pulp fibers.

17. The wipe of claim 14, wherein the fibrous substrate is a composite that contains the absorbent fibers and synthetic thermoplastic fibers.

18. A method for disinfecting a surface, the method comprising contacting the surface with a wipe impregnated with a germicidal solution so that the solution is expressed therefrom, wherein the germicidal solution comprises an antimicrobial quaternary ammonium compound, and wherein the wipe comprises a fibrous substrate on which is disposed a polymer coating, the polymer coating containing a release agent and a cell permeabilizer, wherein the release agent includes a crosslinked polyamideamine and the cell permeabilizer includes a polycationic substance, wherein the crosslinked polyamideamine has a weight average molecular weight of about 1,000,000 to about 2,000,000 grams per mole and the polycationic substance has a weight average molecular weight of about 600,000 to about 1,000,000 grams per mol, and wherein the ratio of the weight average molecular weight of the crosslinked polyamideamine to the weight average molecular weight of the polycationic substance is greater than 1 to about 3.

19. The method of claim 18, wherein the polyamideamine is formed from a polyalkylenepolyamine prepolymer.

20. The method of claim 18, wherein the polyalkylenepolyamine is polyethyleneimine, a polyamine that is grafted with ethyleneimine, or a combination thereof.

21. The method of claim 18, wherein the ratio of the weight average molecular weight of the crosslinked polyamideamine to the weight average molecular weight of the polycationic substance is from about 1.2 to about 1.8.

22. The method of claim 18, wherein the polycationic substance is a polyamine.

23. The method of claim 18, wherein the fibrous substrate contains absorbent fibers.

24. The method of claim 18, wherein about 90% or more of the antimicrobial agent added to the germicidal solution is expressed from the wipe.

25. The method of claim 18, wherein the wipe provides a log reduction of at least about 4 for a gram negative bacteria.

26. The method of claim 25, wherein the gram negative bacteria is *E.Coli*.

\* \* \* \* \*